(12) United States Patent
Burns (10) Patent No.: US 6,957,593 B1
(45) Date of Patent: Oct. 25, 2005

(54) DEVICES, SYSTEMS, AND METHODS FOR ANALYZING SNOW STABILITY

(76) Inventor: Ian F. Burns, 1575 Delucchi La., Suite 222, Reno, NV (US) 89502

( * ) Notice: Subject to any disclaimer, the term of this patent is extended or adjusted under 35 U.S.C. 154(b) by 0 days.

(21) Appl. No.: 10/335,606

(22) Filed: Dec. 31, 2002

Related U.S. Application Data (60) Provisional application No. 60/344,970, filed on Dec. 31, 2001.

(51) Int. Cl.$^7$ .............................................. G01N 33/00
(52) U.S. Cl. ...................................................... 73/866
(58) Field of Search .......................... 73/866, 594, 596, 73/597, 598, 599, 600

(56) References Cited

U.S. PATENT DOCUMENTS

| | | | | |
|---|---|---|---|---|
| 5,661,464 A | * | 8/1997 | Bilak et al. ................. | 340/690 |
| 5,815,064 A | * | 9/1998 | Holmgren et al. ............ | 338/28 |
| 5,831,161 A | * | 11/1998 | Johnson et al. ............. | 73/432.1 |
| 5,864,059 A | * | 1/1999 | Sturm et al. ................ | 73/432.1 |
| 6,530,284 B1 | * | 3/2003 | Tambo et al. ................ | 73/784 |

FOREIGN PATENT DOCUMENTS

| | | | | | |
|---|---|---|---|---|---|
| JP | 11211846 A | * | 8/1999 | ......... | G01W 01/14 |
| JP | 2000081314 A | * | 3/2000 | ........... | G01B 11/06 |

* cited by examiner

*Primary Examiner*—Charles Garber
(74) *Attorney, Agent, or Firm*—Ian F. Burns (57) ABSTRACT

Devices, systems, and methods are disclosed for analyzing various characteristics of snow. In one embodiment of the present invention, a snow sensor is attached to a probe that is inserted beneath the surface of the snow. A depth sensor is provided that measures the depth of the snow sensor as it is operated. The invention can record at least one characteristic of snow as a function of depth.

17 Claims, 5 Drawing Sheets

DEVICES, SYSTEMS, AND METHODS FOR ANALYZING SNOW STABILITY

CROSS REFERENCE TO RELATED APPLICATIONS

This application claims priority of and incorporates by reference U.S. provisional patent application No. 60/344,970, filed on Dec. 31, 2001.

BACKGROUND OF THE INVENTION

1. Field of the Invention

The present invention relates to devices, systems, and methods for analyzing the stability of snow and for forecasting avalanches.

2. Background

An avalanche is the rapid movement of a material down sloped terrain. Most avalanches are primarily composed of snow; however, avalanches may also contain ice, rock, and soil. In general, avalanches occur after snow has been deposited, either by precipitation or by wind, on hills or mountains. When appropriate conditions occur, the snow is suddenly released and the downward rushing snow can release an exceptional amount of energy.

Avalanches have caused a tremendous amount of deaths, injuries, and damage to property. Statistics indicate that the devastating impact of avalanches is rapidly increasing. As the popularity of mountain and winter sports increases, such as backcountry skiing and snow boarding, mountain climbing, and snowmobiling, and the number of people living in or traveling through mountainous area increases, avalanches are killing and injuring more people and destroying more real and personal property.

To date, most advances in avalanche technology have been intended to help those people who have become trapped in avalanches. For example, U.S. Pat. No. 6,484,021 issued to Hereford et al. discloses an example of a radio transceiver that is intended to locate a buried victim. U.S. Pat. No. 5,490,501 issued to Crowley discloses a breathing device that helps an avalanche victim breath when buried in snow. However, there have been very few practical advances in the area of avalanche forecasting. If avalanches could be more easily and accurately forecast, many deaths and injuries could be prevented and the cost of preventing avalanche accidents could be greatly reduced.

There are a number of methods known in the art for determining the risk or likelihood of an avalanche occurring. These techniques include the following structural or physical tests for determining the stability of snow in a particular area: ski pole, hand shear, step, jump, ski traverse, tilt board, cornice, snow pit, compression, shovel shear, ski shear, loaded column, pat, Rutschblock, Rutschkiel, and stuffblock. For example, the Rutschblock and shovel shear tests involve digging a hole in the snow and, crudely, jumping up and down, or pushing the snow sideways with a shovel to judge its strength. These tests are currently widely used to identify weak snow structures.

However, these tests do not measure important variables affecting the likelihood of an avalanche. Although the structural strength of a block of snow can, in some situations, indicate an avalanche risk, the occurrence of an avalanche may depend more on other variables that are not analyzed by these tests. Studies show that the risk of an avalanche is affected by many different factors. Temperature, slope, density, size and shape of snow crystals, hardness, relative humidity, radiation, water content, and other metrological factors can all have a significant influence on avalanche risk. In many cases, these influences increase the probability of an avalanche, so that an area may not be safe even though commonly used tests indicate that it is.

Another problem associated with commonly used tests is that they are difficult and time consuming to perform. A Rutschblock test, for instance, may require a person to exert a significant amount of energy to dig out a pit and perform the test. If a backcountry skier is performing the test, it may be necessary for the skier to put his equipment (skis and backpack) on and off several times. Because of this, most people do not perform the test as much as they should. Furthermore, many people are not sufficiently trained or experienced enough to interpret the results of the test. What has long been needed is a device, system, and method for efficiently and accurately forecasting avalanches.

SUMMARY OF ONE EMBODIMENT OF THE INVENTION

Advantages of One or More Embodiments of the Present Invention

The various embodiments of the present invention may, but do not necessarily, achieve one or more of the following advantages:

- the ability to measure at least one characteristic of snow that can be used to forecast avalanches;
- the ability to measure at least one characteristic of snow as a function of depth;
- the ability to easily and efficiently measure at least one characteristic of snow;
- a ability to measure a plurality of characteristics of snow that can be used to forecast avalanches; and
- the ability to accurately determine the risk of an avalanche.

These and other advantages may be realized by reference to the remaining portions of the specification, claims, and abstract.

Brief Description of One Embodiment of the Present Invention

The present invention comprises a system for analyzing the stability of snow. One embodiment of the system comprises at least one probe, snow sensor, depth sensor, and controller. The probe is configured to be inserted to a plurality of depths beneath a surface of the snow. The snow sensor is attached to the probe and it is configured to sense a characteristic of the snow and produce an output. The depth sensor is being configured to determine a distance the snow sensor is beneath the surface of the snow and produce an output. The controller is in communication with the snow sensor and the depth sensor and it is configured to receive the output from the snow sensor and the output from the depth sensor and determine the characteristic of the snow with respect to distance beneath the surface of the snow.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF AN EMBODIMENT OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figures 1, 2:
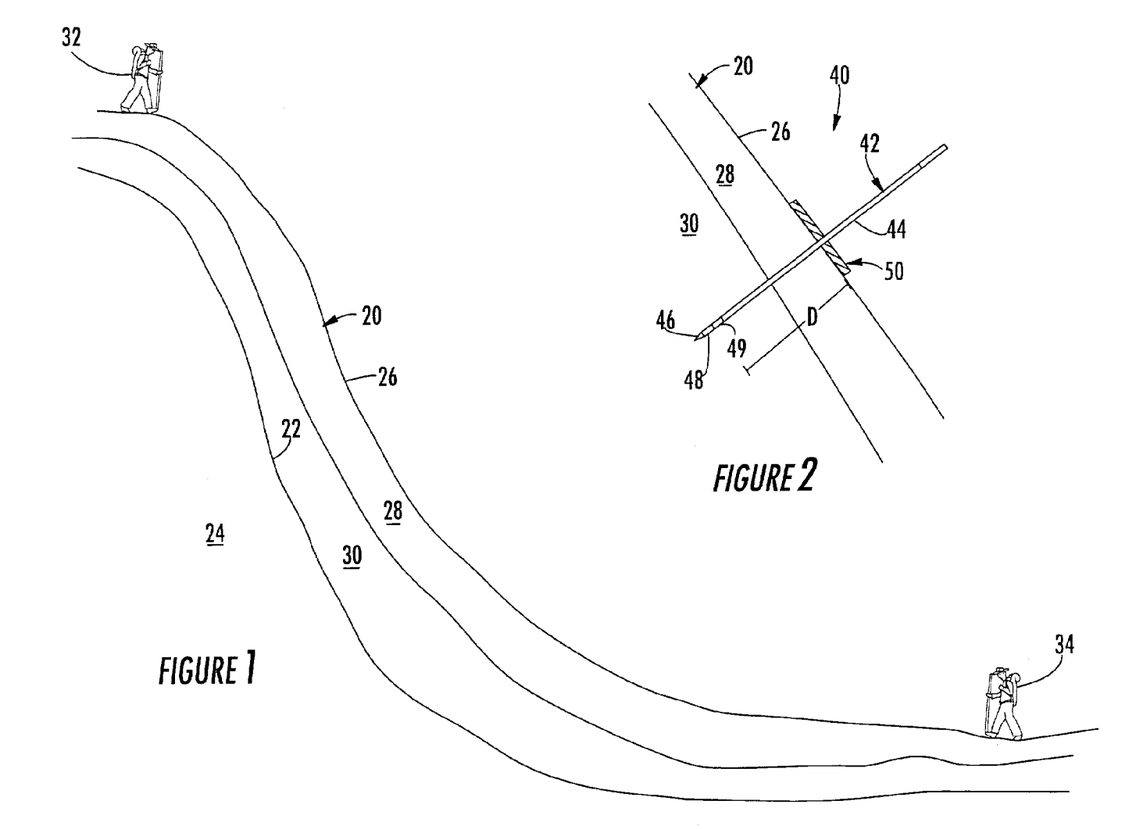
FIG. 1 is substantially a cross sectional side view of a snow covered hillside with potential avalanche conditions.
FIG. 2 is substantially a side view of a probe of one embodiment of the present invention.

FIG. 1, illustrates a typical environment in which the present inventions may be used. Snow 20 has accumulated over a sloped surface 22 of ground 24. Ground 24 may be many different types and sizes of terrain. For example, ground 24 may be a ski slope at a ski resort, a hillside near a transportation route, such as a road or railroad track, or a side of a remote mountain. Snow 20 comprises a surface 26 and may comprise a plurality of layers 28 and 30. The present inventions may be used by a user 32 who is located on or near an area of snow 20 that is to be analyzed or a user 34 who is located a distance away from the area of snow that is to be analyzed. The present inventions may also be used from mobile platforms, such as an aircraft, satellite, or car (not shown) and the present inventions may be configured to be operated autonomously without the need for human users.

Probe

As seen in FIG. 2, one embodiment of the present invention comprises a system, generally indicated by reference number 40. System 40 comprises a probe 42 shown inserted into snow 20. Probe 42 comprises shaft 44, tip 46, and at least one snow sensor 48. Probe 42 may be made from a variety of relatively rigid materials, such as aluminum, fiber glass, or carbon fibers. In backcountry applications it is desirable that probe 42 is relatively light so that it can be easily carried. Preferably, probe 42 comprises a number of interlocking sections (not shown), similar to a rescue avalanche probe. This allows probe 42 to be disassembled for convenient storage and transportation. Probe 42 is preferably at least six feet tall to allow probe to penetrate six feet of snow. It is also desirable that probe 42 have as small a width of less than one inch to allow the probe to penetrate snow more easily. In some embodiments, probe 42 is preferably hollow to allow electrical wires or optical fiber to be placed inside of the probe. As will be discussed below, snow sensor 48 is configured to sense at least one characteristic of snow 20 and produce an output. A surface module 50 may also be provided for performing a number of functions discussed below.

Depth Sensor

Figure 3:
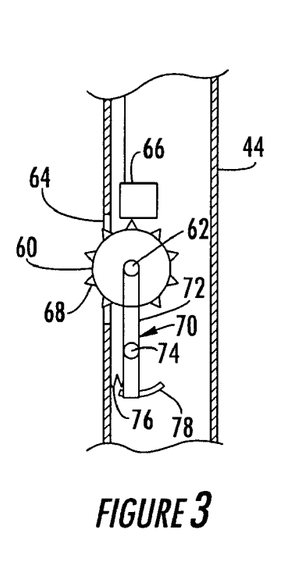
FIG. 3 is substantially a partial cross sectional side view of a wheel sensor of one embodiment of the present invention.

System 40 may also comprise a depth sensor 49 that is configured to determine a distance snow sensor 48 is beneath surface 26 of snow 20 and produce an output. Depth sensor 49 may be many different kinds of depth sensors. As seen in FIG. 3, depth sensor 49 may comprise a wheel 60 that is rotatably attached to shaft 44. Wheel 60 may be positioned at least partially within shaft 44, preferably near snow sensor 48 (see FIG. 2). An opening 64 is provided in shaft 44 that allows at least a portion of wheel 60 to extend out of the shaft. Wheel 60 may be attached to an axle 62 that is positioned inside of shaft 44, perpendicular to a longitudinal axis of the shaft. In normal operation, probe 42 is inserted into snow 20 (see FIG. 2). As wheel 60 comes in contact with snow 20, friction between the snow and the wheel causes the wheel to rotate. One or more grooves, ridges, or fingers 68 may be provided for increasing the amount of friction between snow 20 and wheel 60. As wheel 60 rotates, a rotational sensor 66 senses the rotation and transmits an output signal to a controller (not shown in FIG. 3). Rotational sensor 66 may be many different types of sensors. For example, rotational sensor 66 may be an optical or electromagnetic sensor of a type that is used with computer input deices, such as mice or track balls. The controller is configured to calculate distance from rotation of wheel 60 and determine the depth of sensor 48 beneath surface 26 (see FIG. 2).

A suspension apparatus 70 may be provided for applying a constant amount of force on snow 20 and to prevent damage to wheel 60. Suspension apparatus 70 may comprise an arm 72 that is rotatably attached to axle 62 and a fulcrum 74, and a spring 76. Spring 76 applies a force to arm 72 to rotate the arm around fulcrum 74, thereby biasing wheel 60 in an outward position. If wheel 60 encounters a hard object, such as a rock or ice, suspension apparatus 70 allows the wheel to move inward, thereby avoiding damage.

A position sensor 78 may also be provided for measuring hardness (i.e., resistance to plastic deformation) of snow 20. Position sensor 78 senses the amount arm 72 moves and transmits a signal to a controller (not show in FIG. 3) indicating the arms relative position. Since spring 76 applies a known force to snow 20 through wheel 60, the controller can calculate and compare the relative hardness of snow as wheel 60 moves through the snow. In this way, the depth sensor disclosed in FIG. 3 may also serve as a snow sensor 48.

Figure 4:
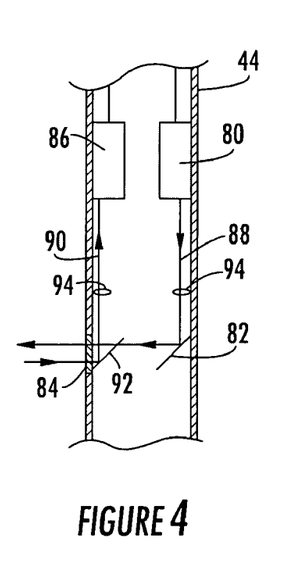
FIG. 4 is substantially a partial cross sectional side view of an optical sensor of one embodiment of the present invention.

FIG. 4 illustrates another embodiment of the depth sensor of the present invention. In this embodiment, a light source 80 is provided inside of shaft 44. Light source 80 may be many different kinds of light sources, such as a light emitting diode or laser diode. The light produced by light source 80 may be in many different wavelengths. In one preferred embodiment, light produced by light source 80 is in the infrared range of light. Light source 80 produces outgoing light 88, which may be focused by a lens 94 and reflected by mirror 82 to optical opening 84. Alternatively, light source 80 may be arranged to transmit light directly out of optical opening 84. Optical opening 84 is a material that is transparent to the wavelength of light that is transmitted by light source 80 and it may comprise a lens for focusing the light a predetermined distance from shaft 44.

As outgoing light 88 is transmitted out of optical opening 84, some of the light is reflected by snow 20 (see FIG. 2) to produce incoming light 90. Incoming light 90 may be reflected by beam splitter 92, through a second lens 94 to photodetector 86. Alternatively, photodetector 86 may be positioned to directly receive incoming light 90.

Naturally occurring variations in the reflective properties of snow 20 (see FIG. 2) create variations in incoming light 90. These variations are caused by different variables, such as the type and density of snow crystals, temperature, water content, density, etc. In normal operation, as probe 42 is inserted into snow 20 (see FIG. 2), the changes in intensity of incoming light 90 are detected by photodetector 86. Photodetector 86 transmits an output signal to a controller (not show in FIG. 4) which can calculate the distance snow sensor 48 has traveled beneath surface 26 (see FIG. 2) by comparing the changes in intensity over a period of time. This embodiment has the advantage of no moving parts. As will be discussed below, this embodiment of the depth sensor may also serve as snow sensor 48.

Figure 5:
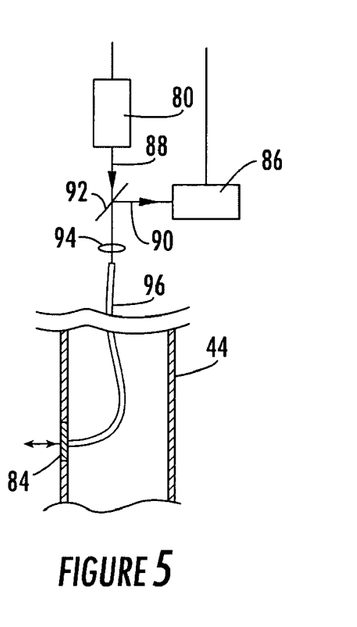
FIG. 5 is substantially a partial cross sectional side view of an optical sensor of another embodiment of the present invention.

FIG. 5 illustrates a different embodiment in which an optical fiber 96 is used to transmit light to optical opening 84. In this embodiment, outgoing light 88 is transmitted through beam splitter 92 and lens 94 to optical fiber 96. The optical fiber 96 transmits the outgoing light 88 to optical opening 84. Incoming light 90 is transmitted by optical fiber 96 to lens 94 and reflected by beam splitter 92 to photodetector 86. This embodiment allows light source 80 and photodetector 86 to be positioned out of shaft 44. This allows a smaller shaft to be used and it places light source 80 and photodetector 86 in a position where they are less likely to be damaged.

Figure 6:
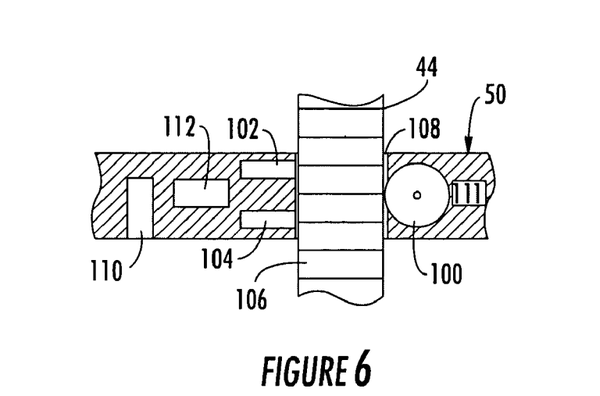
FIG. 6 is substantially a partial cross sectional side view of a probe and surface module of one embodiment of the present invention.

FIG. 6 illustrates a variety of different embodiments of the depth sensor that may be associated with surface module 50. In normal operation, surface module 50 is placed on surface 26 and probe 42 (see FIG. 2) is inserted into hole 108. Probe 42 is then pushed into snow 20. In this embodiment, surface module 50 is large enough to provide a sufficient surface area to prevent surface module 50 to be pressed a significant distance into snow 20. In one embodiment, surface module 50 is incorporated into a ski that is worn by a skier.

Surface module 50 may comprise a wheel 100 that abuts shaft 44 when probe 42 is in hole 108. Wheel 100 is rotatably mounted to surface module 50. Friction between shaft 44 and wheel 100 causes the wheel to rotate. Similar to the embodiment illustrated in FIG. 6, a rotation sensor 111 is provided that is configured to sense the rotation of wheel 100 and transmit output signals to a controller (not shown in FIG. 6). The controller can determine the distance snow sensor 48 is below surface 26 (see FIG. 2) by counting the number of rotations of wheel 100.

Alternatively, surface module 50 may comprise an optical sensor 102 that senses the movement of lines 106. Optical sensor 102 may comprise a light source and a photodetector that can detect the movement of lines 106. Lines 106 have different reflection or absorption properties than the surface of shaft 44. Lines 106 may comprise light absorbent paint and they are preferably evenly spaced along shaft 44. The photodetector detects lines 106 that pass by it and transmits signals to a controller (not shown in FIG. 6). The controller can determine the distance snow sensor 48 is below surface 26 (see FIG. 2) by counting the number of lines that pass by optical sensor 102.

In yet another embodiment, a magnetic sensor 104 is provided. In this embodiment, lines 106 may comprise magnetic paint that produces a small magnetic field. As lines 106 pass by magnetic sensor 104, the sensor senses the magnetic fields and transmits a signal to a controller (not show in FIG. 5). The controller can determine the distance snow sensor 48 is below surface 26 (see FIG. 2) by counting the number of lines that pass by optical sensor 102. Surface module 50 may comprise a variety of sensors 112 for sensing characteristics of snow from surface 26 (see FIG. 2). For example, sensor 112 may be a thermometer configured to sense the surface temperature and or an inclinometer for sensing the slope or angle of surface 26. As will be discussed below, surface module 50 may comprise one or more emitters 110 that are capable of emitting energy, such as light, sound, or radio waves.

Snow Sensor

Figure 7:
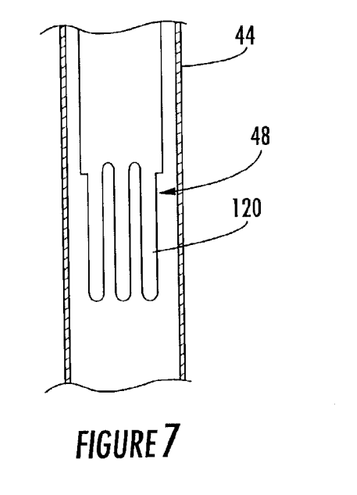
FIG. 7 is substantially a partial cross sectional side view of a hardness sensor of one embodiment of the present invention.

Returning to FIG. 2, snow sensor 48 may be many different kinds of sensors that measure a variety of different characteristics of snow 20. For example, sensor 48 may be configured to sense local characteristics, such as hardness, temperature, or conductivity, of snow 20 as the sensor passes through the snow. As seen in FIG. 7, sensor 48 may comprise a strain gage 120 that is configured to sense strain that is placed on probe 42. Strain gage 120 may be attached directly to an interior surface of shaft 44 or to a carrier sheet that is attached to shaft 44. As probe 42 is inserted into snow 20, resistance in the snow creates a strain in the probe. Strain gage 120 detects the strain and produces an output that can be used to determine the relative hardness of the snow. Strain gage 120 may be any of large number of devices that are well known in the art, such as a wire that produces an electrical resistance that varies with different levels of strain. A plurality of resistive strain elements can be connected in a strain gage bridge circuit to enhance its operation.

To sense temperature, sensor 48 may comprise an electrical thermometer, such as a thermocouple, resistance thermometer, or optical thermometer. In the case of an optical thermometer, the configuration shown in FIGS. 3 and 4 may be used to sense the temperature of snow 20. Conductivity may be measured with a device similar to an ohmmeter using electrodes that are spaced apart on shaft 44.

In another embodiment, sensor 48 comprises an optical sensor. The optical sensor may be the same or similar to the depth sensor illustrated in FIGS. 4 and 5. In this embodiment, a variety of properties of snow 20 can be measured by photodetector 86. For example, photodetector 86 can determine grain shape, grain, size, density, and the presence of free water. It is also noted that different wavelengths of light can be used to analyze different properties of snow 20.

Figure 8:
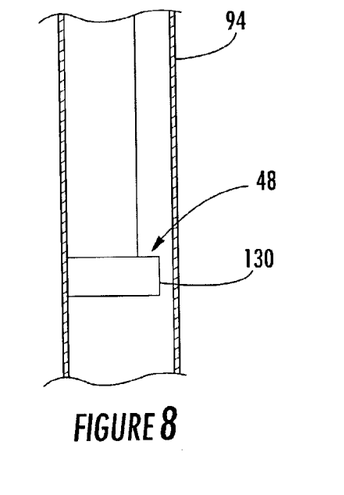
FIG. 8 is substantially a partial cross sectional side view of a sonic sensor of one embodiment of the present invention.

As seen in FIG. 8, sensor 48 may comprise an acoustic sensor 130 that is adapted to emit sound energy and detect reflected sound energy. Acoustic sensor 130 may be any of a large variety of devices that are well known in the art. For example, Acoustic sensor 130 may be an ultrasonic transducer. Ultrasonic transducers convert electrical energy to sound energy above 20 kHz and vice versa. These transducers are generally either magnetostrictive or piezoelectric. Ultrasonic transducers are well known in a variety of areas of technology, such as medical imaging. An ultrasonic image converter may be used in combination with the transducer to produce a cross sectional image of snow 20 (see FIG. 2). As probe 42 is inserted into snow 20, sensor 48 scans the snow at various depths.

Sensor 48 may also comprise sensors that detect energy transmitted from the surface of snow 20. The energy may be many different kinds of energy, such as sound, light, radio waves, or radiation, and the energy may be naturally occurring or man made. For example, a light detector, similar to light detector 86 in FIGS. 4 and 5, may be used to measure the attenuation (absorption) of naturally occurring light, such as sunlight, that falls on surface 26 (see FIG. 2). Alternatively, light may be transmitted by an emitter 108 in surface module 50 of FIG. 6. In this case emitter 108 may be a laser that transmits a predetermined wavelength of light. Sensor 48 may also be an acoustic sensor (microphone) that detects sound produced by emitter 110 (see FIG. 6) or a radio receiver (antenna) that detects radio waves produced by emitter 110. Sensor 48 may also comprise a radiation detector that is configured to detect naturally occurring radiation, such as alpha radiation.

It is recognized that the depth sensor of the present invention may comprise any of the sensors that detect energy transmitted from surface 26 (see FIG. 2). In cases where the energy is produced by emitter 110, the depth of sensor 48 can be determined by measuring the time it takes for the energy to pass from the emitter to the sensor. In the case of naturally occurring energy, depth can be determined by measuring the change in intensity of the energy from the surface to the current location.

The present invention also comprises an embodiment in which snow sensor 48 (see FIG. 2) is used to analyze snow remotely. In this embodiment, snow sensor 48 is a laser or radar emitter that is mounted on a handheld device rather than a probe. Sensor 48 is pointed at a slope that the user wishes to analyze and a beam of energy is transmitted to the slope. The energy is reflected by snow 20 back to sensor 48. It has been found that laser and radar energy can penetrate the surface of most kinds of snow, yet it is reflected by internal structures of the snow. Analyzing the reflected energy can reveal various characteristics of the snow.

Electrical Schematic

Figure 9:
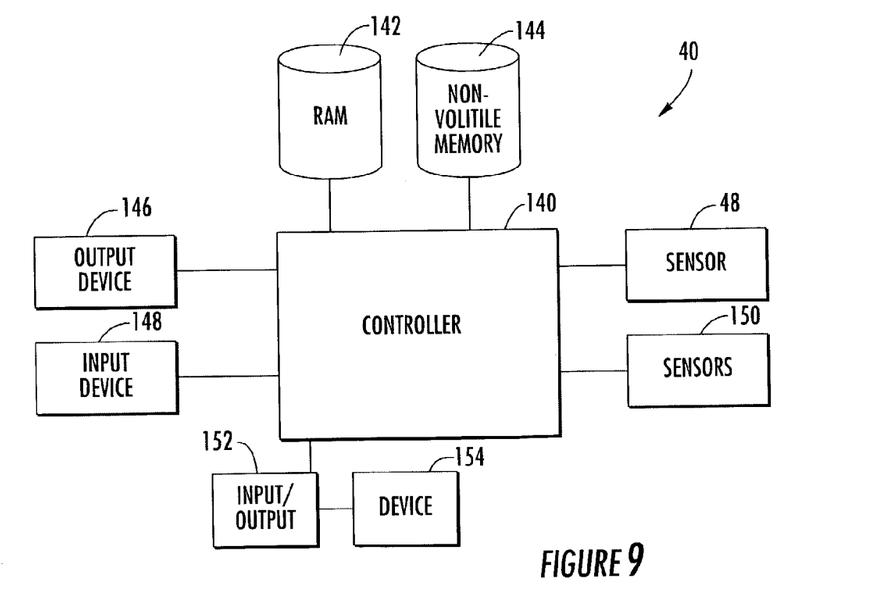
FIG. 9 is substantially a schematic diagram of the electrical components of one embodiment of the present invention.

As seen in FIG. 9, system 40 comprises at least one controller 140 that may be in communication with a random access memory (RAM) 142 and non-volatile memory 144. RAM 142 may be used to execute programs and perform operations. Non-volatile memory 144 may be used to store programs, data, user settings, and other information. Both kinds of memory may be any of a large number of devices that are well known in the art.

System 40 also comprises at least one user output device 146 that is configured to communicate information to a user and a user input device 148 that is configured to allow a user to input information into system 40. Output device 146 may be a visual device, such as a display screen, or an audio device, such as a speaker. A display screen can be used to graphically communicate different snow characteristics. Input device 148 may be a key pad, touch screen, or voice recognition hardware and software. Appropriate interface programs are provided for allowing controller 140 to utilize output device 146 and input device 148.

System 40 also comprises snow sensor 48 in communication with controller 140, which may be any of the snow sensors and/or depth sensors discussed above. System 40 may also comprise additional sensors 150 in communication with controller 140. Sensors 150 may be provided to sense one or more variables that are used by controller 140.

System 40 also comprises snow sensor 48 in communication with controller 140, which may be any of the snow sensors and/or depth sensors discussed above. System 40 may also comprise additional sensors 150 in communication with controller 140. Sensors 150 may be provided to sense variable that are used by controller 140.

System 40 may also comprise input/output device 152 for transmitting and receiving data from an external device 154. For example, device 154 may be a global positioning system unit that provides position information to controller 140. In this case, input/output device 152 may be a serial port. Device 154 may also be a mobile communication device, such as a cellular telephone or radio, and input/output device 132 may be a modem. A mobile communication device could be used to allow system 40 to communicate with computers and other devices over a communication network, such as the Internet.

System 40 may be at least partially implemented on a handheld personal computer. Such devices are well known and a variety of devices could be used to perform many of the functions of the present invention.

Methods

Figures 10, 11:
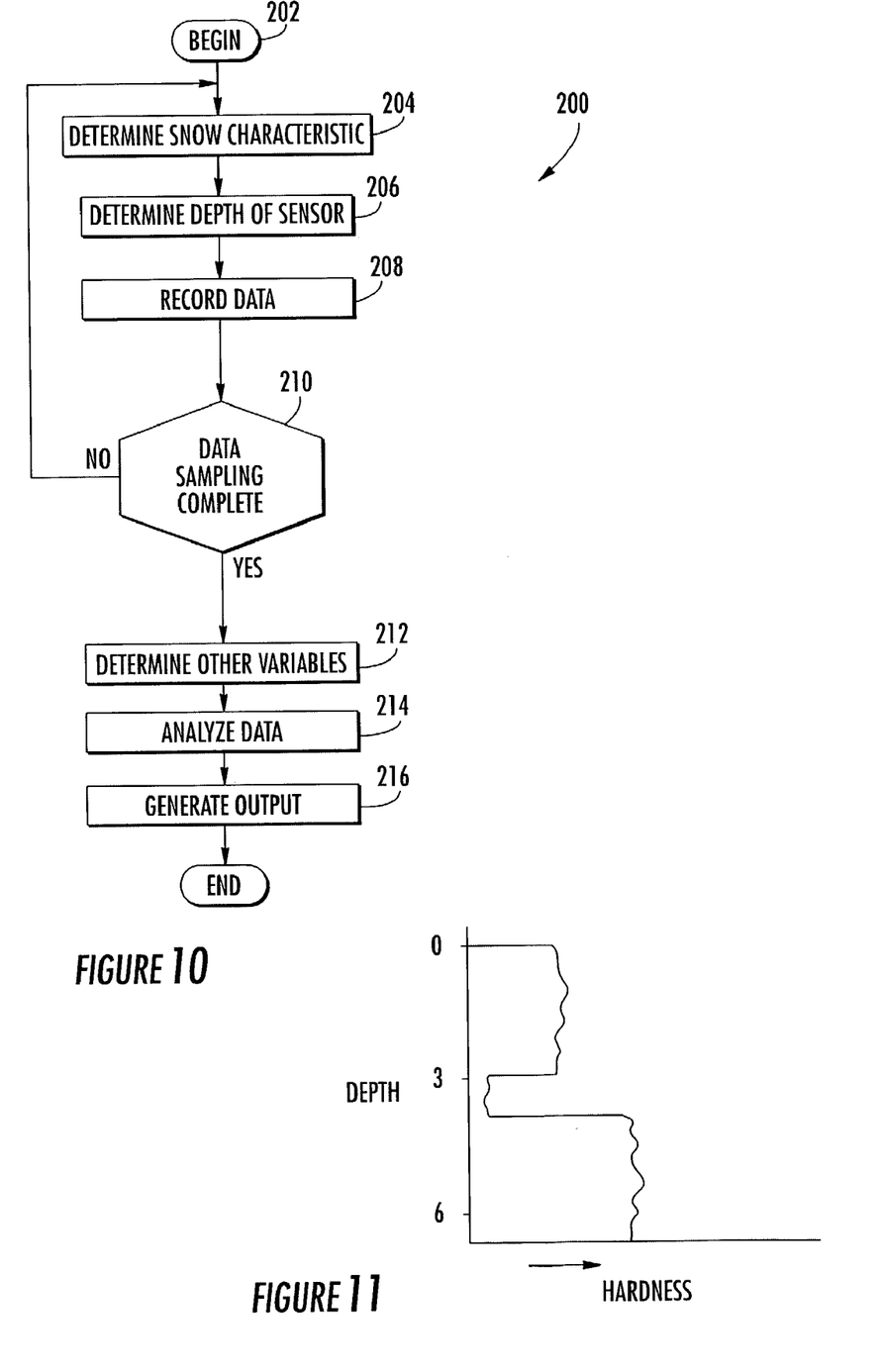
FIG. 10 is substantially a method of the present invention.
FIG. 11 is substantially a graph of hardness versus depth that may be generated by the present invention.

As seen in FIG. 10, the present invention comprises a method analyzing snow stability 202. The method may begin 202 with a user activating a sampling operation. This may be performed by turning system 40 on or pressing an appropriate button. System 40 then determines at least one snow characteristic 204. This may be performed by sensor 48 (see FIG. 2) on probe 42. The snow characteristic may be any of the characteristics discussed above and the characteristic may be sensed by any of the sensors discussed above. If sensor 48 on probe 42 is used to sense the characteristic, then system 40 may also determine the depth D of the sensor 206 at the time the observation is made. This may be performed with any of the sensors or in any of the ways discussed above.

After the snow characteristic and depth is determined, the data may be recorded 208. Method 200 may then determine whether the sampling is complete 210. If sampling is being conducted by sensor 48 on probe 42, then sampling may be complete when the probe is fully inserted in snow 20. System 40 may be able to recognize that the probe is fully inserted from the depth of sensor 48. Alternatively, the user may be required to indicate that sampling is complete by inputting information. If sampling is not complete, method 200 may repeat measurements 204 and 206 and record the data.

Steps 204 to 210 may be repeated in different locations to provide more data. Data from different locations may be averaged to reduce the influence of local anomalies. Furthermore, data from a plurality of locations can be used to derive trends. Position information may be provided from a global positioning system receiver to assist in analysis of the trends.

If sampling is complete, method 200 may determine other variables 212. This may include measuring other variables using other sensors, or it may require the user to input information. For instance, sensors such as inclinometer 112 (see FIG. 6) may be used to determine the slope of the snow or the user may be asked to input observations. The users observations may include many variable that are not easily measured by sensors, such as the presence of visible cracks in the snow, signs of other recent avalanches, recent weather conditions or snow events, etc.

Method 200 may then analyze data 214. Analysis may include many different techniques. For example, well know data filtering and pattern recognition algorithms can be used to condition and analyze the data. An expert analysis system may also be used to derive an overall risk analysis.

Figure 12:
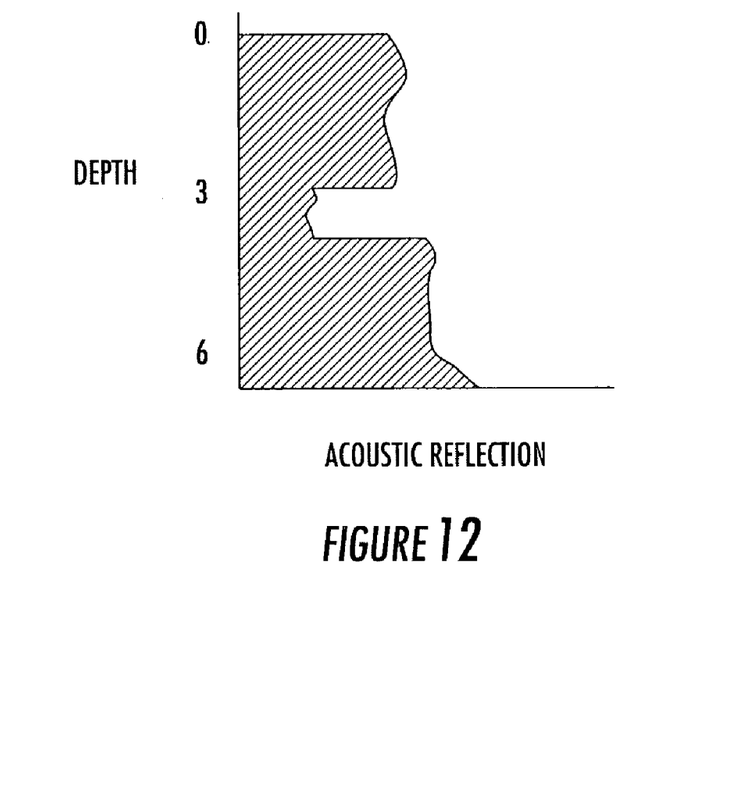
FIG. 12 is substantially a graph of acoustic reflection versus depth that may be generated by the present invention.
Figure 13:
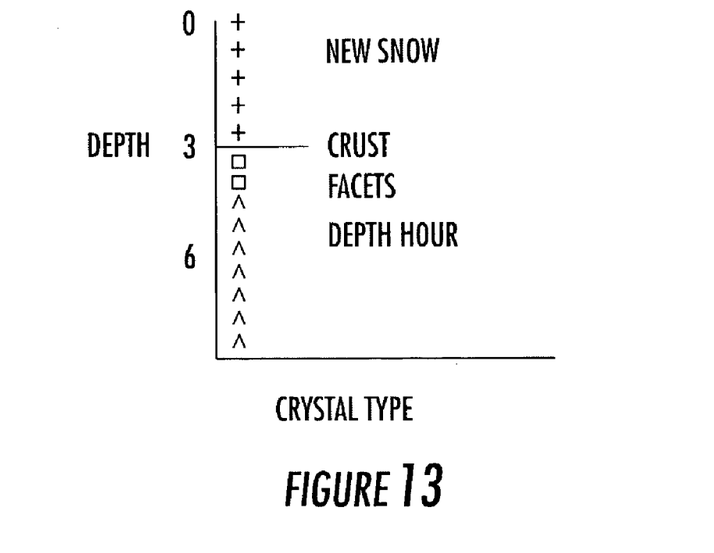
FIG. 13 is substantially a graph of crystal type versus depth that may be generated by the present invention.

Once the data is analyzed, method 200 may generate an output that is useful to the user. One of the most useful outputs is to display a graph of the data. FIG. 11 illustrates a graph of two variables; depth and hardness. Initially as depth increases, hardness remains relatively constant. However, between about three feet and three and a half feet, the hardness of the snow decreases substantially. This may indicate presence of a week layer of snow that creates a high risk of avalanche. FIG. 12 illustrates a graph of acoustic reflection versus depth. Data for this graph may be obtained with sensor 130 of FIG. 8. The graph indicates a relatively constant acoustic reflection characteristic except for a band located at about three feet. Once again, this may indicate the presence of a week layer that could fracture under a load. FIG. 13 illustrates a graph of crystal type versus depth. Data for this graph may be obtained with an optical sensor such as the one disclosed in FIGS. 4 and 5. In this graph, symbols may be used to indicate the location of different types of crystal. The first layer is composed of new snow followed by a thin crust, faceted crystals, and depth hoar. The thin crust and faceted crystals indicate the possible presence of a week bond that is prone to avalanches. It is to be understood that many different types of graphs can be generated using the data collected by the different sensor types of the present invention. A plurality of variables may be included in a single graph to provide more information to the user.

Alternatively, an overall avalanche risk assessment may be presented to the user. For example, a number between one and ten may be calculated and presented to the user. One may be defined as a low avalanche risk and ten may be defined as the highest avalanche risk.

CONCLUSION

Although the description above contains many specifications, these should not be construed as limiting the scope of the invention but as merely providing illustrations of some of presently preferred embodiments of this invention. Thus, the scope of the invention should be determined by the appended claims and their legal equivalents rather than by the examples given.

What is claimed is:

1. A system for analyzing stability of snow, the snow having a plurality of layers, comprising:
   (A) at least one acoustic sensor, the acoustic sensor being configured to:
      (a) emit sound energy, the sound energy being adapted to be reflected differently by the plurality of layers of snow;
      (b) receive sound energy reflected by the plurality of layers of snow; and
      (c) produce an output signal;
   (B) at least one output device, the output device being configured to communicate information to a user; and
   (C) at least one controller in communication with the acoustic sensor and the output device, the controller being configured to:
      (a) cause the acoustic sensor to produce sound energy;
      (b) receive the output signal produced by the acoustic sensor;
      (c) process the output signal to produce layer information; and
      (d) cause the output device to communicate the layer information to a user wherein stability of the snow may be analyzed using the layer information.

2. The system of claim 1 wherein the acoustic sensor comprises at least one ultrasonic transducer.

3. The system of claim 1 wherein the output device comprises at least one display device.

4. The system of claim 3 wherein the display device is configured to display at least one boundary between the plurality of layers.

5. The system of claim 3 wherein the display device is configured to display a graphical representation of the layer information.

6. The system of claim 1 wherein the layer information comprises at least one of the following:
   (A) grain size;
   (B) grain shape;
   (C) hardness;
   (D) strength;
   (E) density;
   (F) water content; and
   (G) liquidity.

7. The system of claim 1 further comprising:
   (A) at least one probe, the probe being configured to be inserted to a plurality of depths beneath a surface of the snow, wherein a sensor is attached to the probe, wherein the sensor is positioned a plurality of depths beneath the surface of the snow when the probe is inserted to a plurality of depths beneath the surface of the snow; and
   (B) at least one depth sensor in communication with the controller, the depth sensor being configured to determine a relative distance the sensor is beneath the surface of the snow and produce an output, the controller being configured to receive the output from the depth sensor and determine the layer information of the snow with respect to distance beneath the surface of the snow.

8. The system of claim 1 further comprising a second sensor in communication with the controller, the second sensor being configured to measure at least one snow characteristic and produce an output, the controller being configured to receive the output from the second sensor and generate stability information using the output from the second sensor.

9. The system of claim 8 wherein the second sensor is configured to measure at least one of the following:
   (A) temperature;
   (B) slope;
   (C) density;
   (D) crystal size;
   (E) crystal shape;
   (F) hardness;
   (G) relative humidity;
   (H) radiation;
   (I) water content;
   (J) liquidity;
   (K) metrological information; and
   (L) conductivity.

10. A system for analyzing the stability of snow, comprising:
- (A) at least one acoustic sensor means for measuring reflection of sound energy at a plurality of depths within the snow;
- (B) at least one controller means for determining layer information from the reflection of sound energy at a plurality of depths within the snow; and
- (C) at least one output means for communicating the layer information to a user.

11. The system of claim 10 further comprising at least one second sensor means for measuring a characteristic of snow without using reflected sound energy.

12. The system of claim 10 further comprising at least one probe means for positioning a sensor beneath the surface of the snow.

13. An apparatus for analyzing stability of snow, comprising:
- (A) an acoustic sensor configured to:
  - (a) generate sound energy, the sound energy capable of being reflected by a plurality of different layers in the snow;
  - (b) transmit the sound energy beneath a surface of the snow;
  - (c) receive sound energy reflected by the plurality of layers of the snow; and
  - (d) generate an output signal, the output signal communicating information related to the sound energy reflected by the plurality of layers of the snow;
- (B) an output device configured to communicate at least layer information to a user; and
- (C) a controller in communication with the acoustic sensor and the output device, the controller configured to:
  - (a) control the acoustic sensor;
  - (b) control the output device;
  - (c) receive and record the output signal;
  - (d) process the output signal to generate the layer information, the layer information comprising layers within the snow; and
  - (e) cause the output device to communicate the layer information wherein a user may detect possible instability of the snow from the layer information.

14. The apparatus of claim 13 wherein the layer information comprises reflection of sound energy as a function of depth.

15. The apparatus of claim 13 wherein the output device is configured to display the layer information in a graphical manner.

16. The apparatus of claim 13 wherein acoustic sensor is configured to generate sound energy in a plurality of different wavelengths.

17. The apparatus of claim 13 wherein the layer information comprises a comparison of a characteristic within each layer of snow.

* * * * *